United States Patent [19]

Kawamura et al.

[11] Patent Number: 5,459,277
[45] Date of Patent: Oct. 17, 1995

[54] IMINOTHIAZOLINES, THEIR PRODUCTION AND USE AS HERBICIDES, AND INTERMEDIATES FOR THEIR PRODUCTION

[75] Inventors: Shinichi Kawamura, Osaka; Keiichi Izumi, Kyogo; Junichi Sato, Osaka; Yuzuru Sanemitsu, Hyogo, all of Japan; Ryo Sato, Durham, N.C.; Tatsuhiro Hamada, Hyogo; Hideyuki Shibata, Osaka, both of Japan

[73] Assignee: Sumitomo Chemical Company, Limited, Osaka, Japan

[21] Appl. No.: 154,509

[22] Filed: Nov. 19, 1993

Related U.S. Application Data

[62] Division of Ser. No. 933,110, Aug. 21, 1992, Pat. No. 5,350,736.

[30] Foreign Application Priority Data

Aug. 23, 1991 [JP] Japan .................... 3-211953

[51] Int. Cl.$^6$ ................................. C07D 277/40
[52] U.S. Cl. ........................... 548/193; 548/199
[58] Field of Search ................... 548/193, 194

[56] References Cited

U.S. PATENT DOCUMENTS

| | | |
|---|---|---|
| 4,103,017 | 7/1978 | Davies et al. . |
| 4,913,722 | 4/1990 | Felix et al. . |

FOREIGN PATENT DOCUMENTS

| | | |
|---|---|---|
| 941288 | 7/1949 | European Pat. Off. . |
| 300906 | 7/1988 | European Pat. Off. . |
| 349283 | 6/1989 | European Pat. Off. . |
| 349282 | 6/1989 | European Pat. Off. . |
| 432600 | 12/1989 | European Pat. Off. . |
| 384244 | 2/1990 | European Pat. Off. . |
| 0446802 | 9/1991 | European Pat. Off. . |

OTHER PUBLICATIONS

McOmie, Protective Groups in Organic Chemistry pp. 46–59 (1973).

*Primary Examiner*—Robert Gerstl
*Attorney, Agent, or Firm*—Birch, Stewart, Kolasch & Birch

[57] ABSTRACT

There is disclosed an iminothiazoline compound of the formula:

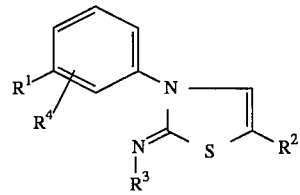

(I)

wherein $R^1$ is halogen, halo(lower)alkyl, halo(lower)alkoxy or halo(lower)alkylthio; $R^2$ is lower alkyl, chlorine, bromine or iodine; $R^3$ is (lower alkyl)carbonyl, (lower cycloalkyl)carbonyl, (lower cycloalkoxy)carbonyl, (lower alkoxy)carbonyl or (lower alkyl)sulfonyl, all of which are optionally substituted with at least one substituent selected from halogen, lower alkyl, lower alkoxy, lower cycloalkyl and lower cycloalkoxy; and $R^4$ is halogen. Also disclosed are a process for producing this compound, a herbicidal composition comprising this compound as an active ingredient, and a method for controlling undesired weeds by use of this compound as a herbicide.

5 Claims, No Drawings

IMINOTHIAZOLINES, THEIR PRODUCTION AND USE AS HERBICIDES, AND INTERMEDIATES FOR THEIR PRODUCTION

This application is a divisional of application Ser. No. 07/933,110, filed on Aug. 21, 1992, U.S. Pat. No. 5,350,736 the entire contents of which are hereby incorporated by reference.

FIELD OF THE INVENTION

The present invention relates to iminothiazolines, their production and use as herbicides, and intermediates for their production. More particularly, it relates to iminothiazoline compounds having strong herbicidal potency and intermediate compounds for production of the iminothiazoline compounds.

BACKGROUND OF THE INVENTION

Certain kinds of iminothiazolidine derivatives are known to be useful as an active ingredient of herbicidal compositions (cf., EP-A-0349282). However, they can hardly be said to be satisfactory herbicides.

OBJECTS OF THE INVENTION

The present inventors have intensively studied to seek satisfactory herbicides and found that particular iminothiazoline compounds have strong herbicidal potency and some of them further exhibit noticeable selectivity between crop plants and weeds.

SUMMARY OF THE INVENTION

The present invention provides iminothiazoline compounds of the formula:

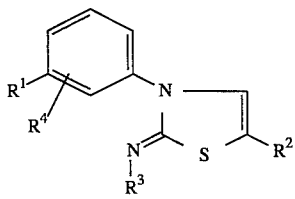

(I)

wherein $R^1$ is halogen, halo(lower)alkyl, halo(lower)alkoxy or halo(lower)alkylthio; $R^2$ is lower alkyl, chlorine, bromine or iodine; $R^3$ is (lower alkyl)carbonyl, (lower cycloalkyl)carbonyl, (lower alkoxy)carbonyl, (lower cycloalkoxy)carbonyl or (lower alkyl)sulfonyl, all of which are optionally substituted with substituents which are the same or different and are selected from halogen, lower alkyl, lower alkoxy, lower cycloalkyl and lower cycloalkoxy; and $R^4$ is halogen; more specifically, iminothiazoline compounds of the formula (I) wherein $R^1$ is halogen, halo($C_1$-$C_3$)alkyl, halo($C_1$-$C_3$)alkoxy or halo($C_1$-$C_3$)alkylthio; $R^2$ is $C_1$-$C_2$ alkyl chlorine bromine or iodine; $R^3$ is $C_1$-$C_6$ alkylcarbonyl, $C_3$-$C_6$ cycloalkylcarbonyl, $C_1$-$C_6$ alkoxycarbonyl, $C_3$-$C_6$ cycloalkoxycarbonyl or $C_1$-$C_6$ alkylsulfonyl, all of which are optionally substituted with substituents which are the same or different and are selected from halogen, $C_1$-$C_3$ alkyl, $C_1$-$C_3$ alkoxy, $C_3$-$C_6$ cycloalkyl and $C_3$-$C_6$ cycloalkoxy; and $R^4$ is halogen; an iminothiazoline compound of the formula:

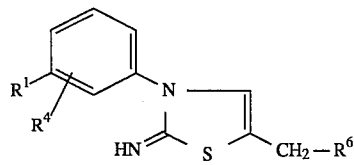

(IV)

wherein $R^1$ and $R^4$ are each as defined above and $R^6$ is hydrogen or methyl, which is an intermediate for the compound (I); a process for producing the iminothiazoline compound (IV); and a herbicidal composition comprising as an active ingredient the above iminothiazoline compounds (I).

DETAILED DESCRIPTION OF THE INVENTION

As used herein, the term "$C_n$-$C_m$" refers to the carbon number of a group immediately following this term. In case of $C_1$-$C_6$ alkylcarbonyl, for instance, the term "$C_1$-$C_6$" indicates the carbon number of its alkyl portion and exclude that of its carbonyl portion. Also, a group substituted with a substituent preferably covers a group bearing from 1 to 10 substituents which may be the same or different.

The iminothiazoline compounds (I)produce generally strong herbicidal activity against a wide variety of weeds including broad-leaved weeds and Graminaceous weeds in agricultural plowed fields by foliar or soil treatment without producing any material phytotoxicity to crop plants. Examples of the broad-leaved weeds include common purslane (Portulaca oleracea), common chickweed (Stellaria media), common lambsquarters (Chenopodium album), redroot pigweed (Amaranthus retroflexus), radish (Raphanus sativus), wild mustard (Sinapis arvensis), shepherdspurse (Capsella bursa-pastoris), hemp sesbania (Sesbania exaltata), sicklepod (Cassia obtusifolia), velvetleaf (Abutilon theophrasti), prickly sida (Sida spinosa), field pansy (Viola arvensis), catchweed bedstraw (Galium aparine), ivyleaf morningglory (Ipomoea hederacea), tall morningglory (Ipomoea purpurea), field bindweed (Convolvulus arvensis), purple deadnettle (Lamium purpureum), henbit (Lamium amplexicaure), jimsonweed (Datura stramonium), black nightshade (Solanum nigrum), persian speedwell (Veronica persica), common cocklebur (Xanthium pensylvanicum), common sunflower (Helianthus annuus), scentless chamomile (Matricaria perforata) and corn marigold (Chrysanthemum segetum). Examples of Graminaceous weeds include Japanese millet (Echinochloa frumentacea), barnyardgrass (Echinochloa crus-galli), green foxtail (Setaria viridis), yellow foxtail (Setaria glauca), southern crabgrass (Digitaria ciliaris), large crabgrass (Digitaria sanguinalis), annual bluegrass (Poa annua), blackgrass (Alopecurus myosuroides), oats (Arena sativa), wild oats (Avena fatua), johnsongrass (Sorghum halepense ), quackgrass (Agropyron repens ), downy brome (Bromus tectorum), giant foxtail (Setaria faberi), fall panicum (Panicum dichotomiflorum), shattercane (Sorghum bicolor) and bermudagrass (Cynodon dactylon). Some of the iminothiazoline compounds (I) have the advantage of showing no material chemical injury to various agricultural crops such as corn, wheat, barley, rice plant, soybean, cotton and sugar beet.

The iminothiazoline compounds (I) are also effective in exterminating paddy field weeds including Graminaceous weeds such as barnyardgrass (Echinochloa oryzicola), broad-leaved weeds such as common falsepimpernel (*Lindernia procumbens*), indian toothcup (*Rotala indica*), waterwort (*Elatine triandra*) and *Ammannia multiflora*, Cyperaceous weeds such as umbrella sedge (*Cyperus difformis*), hardstem bulrush (*Scirpus juncoides*), needle spikerush (*Eleocharis acicularis*) and water nutgrass (*Cyperus serotinus*), and others such as monochoria (*Monochoria vaginalis*) and arrowhead (*Sagittaria pygmaea*). Some of the iminothiazoline compounds (I) have the advantage of showing no phytotoxicity to rice plants on flooding treatment.

Among the iminothiazoline compounds (I), preferred are those wherein $R^1$ is halo $(C_1-C_3)$ alkyl, more preferably trifluoromethyl; those wherein $R^2$ is methyl or ethyl; those wherein $R^3$ is $C_1-C_6$ alkylcarbonyl or $C_3-C_6$ cycloalkylcarbonyl, both of which are optionally substituted with at least one substituent selected from halogen, $C_1-C_3$ alkyl and $C_1-C_3$ alkoxy; and those wherein $R^4$ is present at the para position, more particularly fluorine at the para position.

The iminothiazoline compounds (I) can be produced by various procedures, of which typical examples are shown in the following schemes I to III.

Scheme II

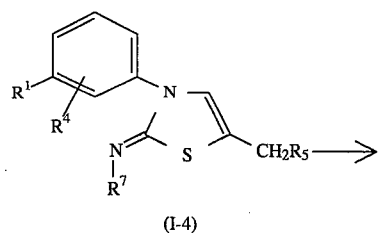

(I-4)

Scheme I

-continued
Scheme II

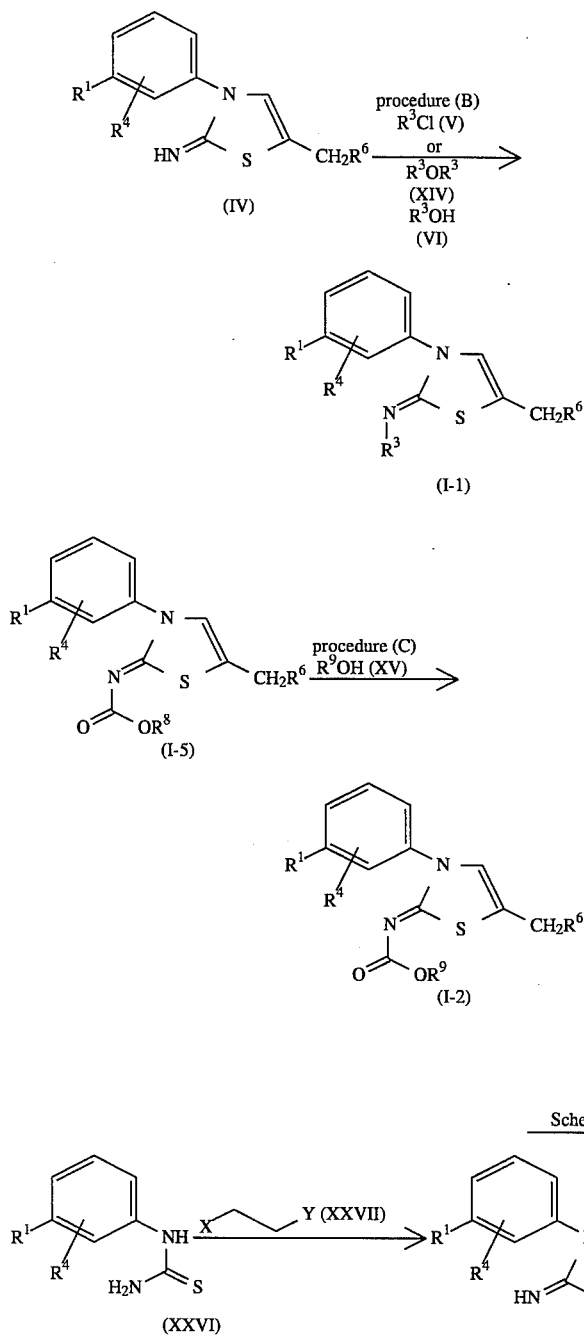

wherein $R^1$, $R^2$, $R^3$, $R^4$ and $R^6$ are each as defined above; $R^7$ is ($C_1$–$C_6$ alkyl) carbonyl; $R^8$ and $R^9$, which are different, are $C_1$–$C_6$ alkyl; $R^{10}$ is chlorine, bromine or iodine; and X and Y are each bromine or iodine.

Procedures for production of the iminothiazoline compounds (I) as shown in the above schemes I to III will hereinafter be explained in detail.

Procedure (A):

The iminothiazoline compound (I) wherein is $R^2$ is methyl or ethyl can be obtained by reacting the iminithiazolidine compound (II) with a base or acid.

This reaction is usually carried out in a solvent at a temperature of about 0° to 200° C. for a period of 1 to 30 hours. The base or acid is used at a proportion of 1 to 100 equivalents to one equivalent of the compound (II).

As the solvent, there may be exemplified aliphatic hydrocarbons (e.g., hexane, heptane), aromatic hydrocarbons (e.g., benzene, toluene, xylene), ethers (e.g., diisopropyl ether, dioxane, tetrahydrofuran, diethylene glycol dimethyl ether), alcohols (e.g., methanol, ethanol, isopropanol, t-butanol, octanol, cyclohexanol, 2-methoxyethanol, diethylene glycol, glycerin), acid amides (e.g, N,N-dimethylformamide) and sulfur compounds (e.g, dimethylsulfoxide, sulforan). These solvents may be used solely or in combination. Examples of the base are inorganic bases (e.g., sodium hydroxide, potassium hydroxide, sodium carbonate, potassium carbonate, sodium hydride) and alkali metal alkoxides (e.g., sodium methoxide, sodium ethoxide, potassium t-butoxide, sodium t-butoxide). Examples of the acid are sulfuric acid and hydrochloric acid.

After completion of the reaction, the reaction mixture may be subjected to ordinary post-treatment in a per se conventional manner such as extraction with an organic solvent and concentration. If necessary, any purification method (e.g., chromatography, recrystallization) may be further utilized to give the objective compound (I), i.e., compound (I-1).

Procedure (B):

The iminothiazoline compound (I) wherein $R^2$ is methyl or ethyl can be obtained by the reaction of the iminothiazoline compound (IV) with an acid chloride (V) or acid anhydride (XIV) in the presence of a base, or by the reaction Scheme III

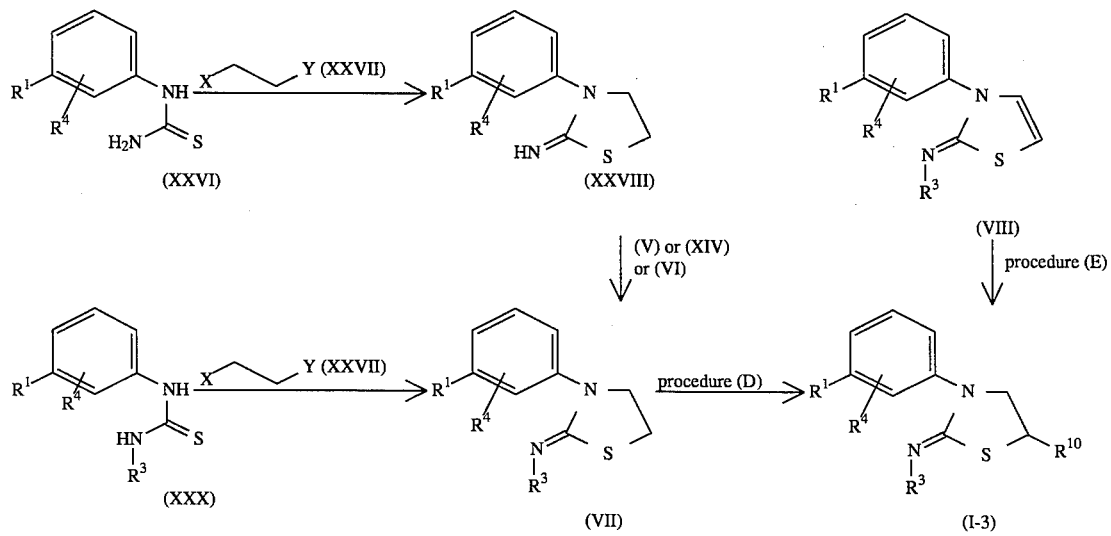

of the iminothiazoline compound (IV) with an acid (VI).

This reaction is usually carried out in a solvent at a temperature of about 0° to 200° C. for a period of 1 to 30 hours. The acid chloride (V), acid anhydride (XIV) or acid (VI) may be used at a proportion of 1 to 10 equivalents to one equivalent of the compound (IV), and the base may be used at a proportion of 1 to 50 equivalents to one equivalent of the compound (IV). When the reaction is carried with the acid (VI), a condensing agent such as dicyclohexylcarbodiimide is usually used at a proportion of 1 to 10 equivalents to one equivalent of the compound (IV).

As the solvent, there may be exemplified aliphatic hydrocarbons (e.g., hexane, heptane, ligroin, petroleum ether), aromatic hydrocarbons (e.g., benzene, toluene, xylene), halogenated hydrocarbons (e.g., chloroform, carbon tetrachloride, dichloroethane, chlorobenzene, dichlorobenzene), ethers (e.g., diethyl ether, diisopropyl ether, dioxane, tetrahydrofuran, diethylene glycol dimethyl ether), ketones (e.g., acetone, methyl ethyl ketone, methyl isobutyl ketone, isophorone, cyclohexanone), esters (e.g., ethyl formate, ethyl acetate, butyl acetate, diethyl carbonate), nitro compounds (e.g., nitroethane, nitrobenzene), nitriles (e.g., acetonitrile, isobutyronitrile), tertiary amines (e.g., pyridine, triethylamine, N,N-diethylaniline, tributylamine, N-methylmorpholine), acid amides (e.g., N,N-dimethylformamide) and sulfur compounds (e.g, dimethylsulfoxide, sulforan). These solvents may be used solely or in combination. Examples of the base are organic bases (e.g., pyridine, triethylamine, N,N-diethylaniline) or inorganic bases (e.g., potassium carbonate, sodium hydroxide).

After completion of the reaction, the reaction mixture may be subjected to ordinary post-treatment in the same manner as described in Procedure (A) to give the objective compound (I), i.e., compound (I-1).

Procedure (C):

The iminothiazoline compound (I) wherein $R^2$ is methyl or ethyl and $R^3$ is —CO—$OR^9$ can be produced by reacting the iminothiazoline compound (I-5) with the alcohol (XV) in the presence of a base.

This reaction is usually carried out in a solvent at a temperature of about 10° to 200° C. for a period of 1 to 100 hours. The alcohol (XV) and base may be used at proportions of 1 to 10 equivalents and 0.5 to 50 equivalents to one equivalent of the compound (I-5), respectively.

As the solvent, there may be exemplified aliphatic hydrocarbons (e.g., hexane, heptane, ligroin), aromatic hydrocarbons (e.g., benzene, toluene, xylene), ethers (e.g., diethyl ether, diisopropyl ether, dioxane, tetrahydrofuran, diethylene glycol dimethyl ether), alcohols (e.g., methanol, ethanol, isopropanol, t-butanol, octanol, cyclohexanol, 2-methoxyethanol, diethylene glycol, glycerin), acid amides (e.g, N,N-dimethylformamide), sulfur compounds (e.g, dimethylsulfoxide, sulforan) and water. These solvents may be used solely or in combination. Examples of the base are inorganic bases (e.g., sodium hydroxide, potassium hydroxide) and alkali metal alkoxides (e.g., sodium methoxide, sodium ethoxide).

After completion of the reaction, the reaction mixture may be subjected to ordinary post-treatment in the same manner as described in Procedure (A) to give the objective compound (I), i.e., compound (I-2).

Procedure (D):

The iminothiazoline compound (I) wherein $R^2$ is chlorine, bromine or iodine is prepared by reacting the iminothiazolidine compound (VII) with a chlorinating, brominating or iodinating agent.

This reaction is usually carried out in a solvent at a temperature of about 50° to 150° C. for a period of 2 to 100 hours. The chlorinating, brominating or iodinating agent may be used at a proportion of 1 to 10 equivalents to one equivalent of the compound (VII).

Examples of the solvent are aliphatic hydrocarbons (e.g., hexane, heptane), aromatic hydrocarbons (e.g., benzene, toluene, xylene), halogenated hydrocarbons (e.g., chloroform, carbon tetrachloride, dichloroethane) and ethers (e.g., diisopropyl ether, dioxane, tetrahydrofuran, diethylene glycol dimethyl ether). These solvents may be used solely or in combination. As the chlorinating, brominating or iodinating agent, there may be exemplified N-chlorosuccinimide, N-bromosuccinimide and N-iodosuccinimide.

After completion of the reaction, the reaction mixture may be subjected to ordinary post-treatment in the same manner as described in Procedure (A) to give the objective compound (I), i.e., compound (I-3).

Procedure (E):

The iminothiazoline compound (I) wherein $R^2$ is chlorine, bromine or iodine can be obtained by reacting the iminothiazoline compound (VIII) with a chlorinating, brominating or iodinating agent.

This reaction is usually carried out in a solvent at a temperature of about 50° to 150° C. for a period of 2 to 100 hours. The chlorinating, brominating or iodinating agent may be used at a proportion of 1 to 10 equivalents to one equivalent of the compound (VIII).

Examples of the solvent and chlorinating, brominating or iodinating agent may be those as exemplified in Procedure (D).

After completion of the reaction, the reaction mixture may be subjected to ordinary post-treatment in the same manner as described in Procedure (A) to give the objective compound (I), i.e., compound (I-3).

Typical examples of the iminothiazoline compounds (I) produced by the above procedure are shown in Table 1.

TABLE 1

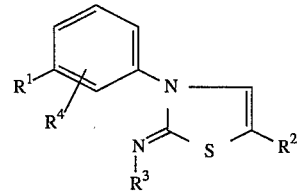

(I)

| $R^1$ | $R^2$ | $R^3$ | $R^4$ |
|---|---|---|---|
| $CF_3$ | $CH_3$ | $COCH_3$ | 4-F |
| $CF_3$ | $CH_3$ | $COCF_3$ | 4-F |
| $CF_3$ | $CH_3$ | $CO\text{-}i\text{-}C_3H_7$ | 4-F |
| $CF_3$ | $CH_3$ | $CO_2\text{-}i\text{-}C_3H_7$ | 4-F |
| $CF_3$ | $CH_3$ | $COCF_3$ | 6-F |
| $CF_3$ | $CH_3$ | $CO_2\text{-}i\text{-}C_3H_7$ | 6-F |
| $CF_3$ | $CH_3$ | $COCH_3$ | 4-Cl |
| $CF_3$ | $CH_3$ | $COCF_3$ | 4-Cl |
| $CF_3$ | $CH_3$ | CO—◁—$CH_3$ | 4-Cl |
| Cl | $C_2H_5$ | $CO_2$—◁ | 4-F |
| Br | Br | $CO_2\text{-}n\text{-}C_4H_9$ | 5-F |

TABLE 1-continued (I) structure: aryl(R¹,R⁴)-N=C(NR³)-S-C=C-R²

| R¹ | R² | R³ | R⁴ |
|---|---|---|---|
| $CF_3$ | $C_2H_5$ | $COCH_2OCH_3$ | 2-F |
| $OCF_3$ | $CH_3$ | $COCF_3$ | 4-F |
| $SCF_3$ | $CH_3$ | $COCF_3$ | 4-F |
| $OCHF_2$ | Br | CO-cyclopropyl | 4-F |
| $CF_3$ | Cl | $CO$-n-$C_3H_7$ | 4-F |
| $CF_3$ | I | $CO$-n-$C_5H_{11}$ | 2-F |
| $CF_3$ | $CH_3$ | CO-cyclopropyl | 4-Cl |
| $CF_3$ | $CH_3$ | $COCHF_2$ | 4-F |
| $CF_3$ | $C_2H_5$ | $COCH_3$ | 4-F |
| $CF_3$ | $C_2H_5$ | $COCF_3$ | 4-F |
| $CF_3$ | $C_2H_5$ | $COCHF_2$ | 4-F |
| Cl | Br | $CO_2C_2H_5$ | 4-F |
| $CF_3$ | $CH_3$ | $COCH_2$-t-$C_4H_9$ | 4-F |
| $CF_3$ | $CH_3$ | $CO$-n-$C_5H_{11}$ | 4-F |
| $CF_3$ | $CH_3$ | $COCH_2CH_2Cl$ | 4-F |
| $CF_3$ | $CH_3$ | $COCH_2OCH_3$ | 4-F |
| $CF_3$ | $CH_3$ | CO-cyclohexyl | 4-Cl |
| $CF_3$ | $CH_3$ | $COC_3H_7$ | 4-Cl |
| $CF_3$ | $CH_3$ | $SO_2CF_3$ | 4-Cl |
| $CF_3$ | $CH_3$ | $CO_2$-n-$C_6H_{13}$ | 4-F |
| $CF_3$ | $CH_3$ | CO-(2-methylcyclopropyl) | 4-F |
| $CF_3$ | $CH_3$ | $SO_2CH_3$ | 4-Cl |
| $CF_3$ | $CH_3$ | $CO_2CH_2CH_2OCH_3$ | 4-Cl |
| $CF_3S$ | $CH_3$ | $CO_2$-cyclopropyl | 4-F |
| $CHF_2O$ | $CH_3$ | $CO_2$-cyclopentyl | 4-F |
| $CF_3$ | $CH_3$ | $CO_2$-cyclohexyl | 4-F |
| Cl | Br | $CO_2$-n-$C_6H_{13}$ | 4-F |
| Br | $CH_3$ | $CO_2$-i-$C_3H_7$ | 4-Cl |
| $CF_3$ | $CH_3$ | $CO_2C_4H_9$ | 4-Cl |
| $CF_3$ | $CH_3$ | $COCH_2$-cyclopropyl | 4-Cl |
| $CF_3$ | $C_2H_5$ | $COCH_2O$-cyclopentyl | 4-F |
| $CF_3$ | $CH_3$ | $CO_2CH_2CH_2O$-cyclohexyl | 4-F |
| $CF_3$ | $CH_3$ | $CO$-n-$C_6H_{13}$ | 4-F |
| $C_2F_5$ | $CH_3$ | $CO$-n-$C_3H_7$ | 4-F |
| $CF_2HCF_2O$ | $CH_3$ | $COC_2H_5$ | 4-F |
| $C_2F_5S$ | $CH_3$ | $COCH_3$ | 4-F |
| $CF_3$ | $CH_3$ | $SO_2C_3H_7$ | 4-F |
| $CF_3$ | $CH_3$ | CO-(3,5-dimethylcyclohexyl) | 4-F |
| $CF_3$ | $CH_3$ | COCHCl-cyclopropyl | 4-F |

It should be noted that the iminothiazoline compounds (I) include their stereo isomers having herbicidal activity.

The iminothiazoline compounds (II) can be obtained by reacting the aniline derivatives (IX) with the isothiocyanate (X) to give the thiourea (XI) which is then converted into the compound (II) (Scheme I).

This reaction is usually carried out in a solvent at a temperature of about 0° to 200° C. for a period of 1 to 30 hours. The compound (X) may be used at proportions of 1 to 5 equivalents to one equivalent of the compound (IX).

As the solvent, there may be exemplified aliphatic hydrocarbons (e.g., hexane, heptane, ligroin, petroleum ether), aromatic hydrocarbons (e.g., benzene, toluene, xylene), halogenated hydrocarbons (e.g., chloroform, carbon tetrachloride, dichloroethane, chlorobenzene, dichlorobenzene), ethers (e.g., diethyl ether, diisopropyl ether, dioxane, tetrahydrofuran, diethylene glycol dimethyl ether), ketones (e.g., acetone, methyl ethyl ketone, methyl isobutyl ketone, isophorone, cyclohexanone), nitro compounds (e.g., nitroethane, nitrobenzene), tertiary amines (e.g., N,N-diethylaniline, tributylamine, N-methylmorpholine), acid amides (e.g., N,N-dimethylformamide) and sulfur compounds (e.g., dimethylsulfoxide, sulforan). These solvents may be used solely or in combination. As the catalyst which may be used for converting the compound (XI) into the compound (II), there may be exemplified acids (e.g., trifluoroacetic acid, sulfuric acid) and bases (e.g., sodium methylate).

After completion of the reaction, the reaction mixture may be subjected to ordinary post-treatment in the same manner as described in Procedure (A) to give the objective compound (II).

According to this method, the compound (I-1) can be directly obtained without isolation of the compound (II).

The compound (II) can also be produced by reacting the iminothiazolidine compound (III) with a base.

This reaction is usually carried out in a solvent at a temperature of about 0° to 200° C. for a period of 1 to 30 hours. The base may be used at proportions of 1 to 50 equivalents to one equivalent of the compound (III).

As the solvent, there may be exemplified aliphatic hydrocarbons (e.g., hexane, heptane, ligroin), aromatic hydrocarbons (e.g., benzene, toluene, xylene), ethers (e.g., diethyl ether, diisopropyl ether, dioxane, tetrahydrofuran, diethylene glycol dimethyl ether), alcohols (e.g., methanol, ethanol, isopropanol, t-butanol, octanol, cyclohexanol, 2-methoxyethanol, diethylene glycol, glycerin), acid amides (e.g., formamide, N,N-dimethylformamide, acetamide) and sulfur compounds (e.g., dimethylsulfoxide, sulforan). These solvents may be used solely or in combination. Examples of the base may be inorganic bases (e.g., sodium hydroxide, potassium hydroxide) and alkali metal alkoxides (e.g., sodium methoxide, sodium ethoxide, sodium t-butoxide).

After completion of the reaction, the reaction mixture may be subjected to ordinary post-treatment in the same manner as described in Procedure (A) to give the objective compound (II).

According to this method, the compound (I-1) can also be directly obtained without isolation of the compound (II).

The compound (VIII) can be obtained by reacting the iminothiazoline compound (I-3) wherein $R^{10}$ is bromine with a reducing agent such as tributyltin hydride.

This reaction is usually carried out in a solvent at a temperature of about 0° to 200° C. for a period of 1 to 30 hours. The reducing agent may be used at proportions of 1 to 100 equivalents to one equivalent of the compound (I-3) wherein $R^{10}$ is bromine.

There may be used as the solvent aliphatic hydrocarbons (e.g., hexane, heptane, ligroin, petroleum ether), aromatic hydrocarbons (e.g., benzene, toluene, xylene), ethers (e.g., diethyl ether, diisopropyl ether, dioxane, tetrahydrofuran, diethylene glycol dimethyl ether), ketones (e.g., acetone, methyl ethyl ketone, methyl isobutyl ketone, isophorone, cyclohexanone), esters (e.g., ethyl formate, ethyl acetate, butyl acetate, diethyl carbonate), nitro compounds (e.g., nitroethane, nitrobenzene), nitriles (e.g., acetonitrile, isobutyronitrile), acid amides (e.g., N,N-dimethylformamide) and sulfur compounds (e.g., dimethylsulfoxide, sulforan). These solvents may be used solely or in combination.

After completion of the reaction, the reaction mixture may be subjected to ordinary post-treatment in the same manner as described in Procedure (A).

The iminothiazolidine compound (III) may be produced by the method as described in J. Am. Chem. Soc., 1079(1984). That is, the compound (III) can be obtained by reacting the aniline compound (XVI) with the isothiocyanate compound (X) to give the thiourea compound (XVII) which is then treated with a halogenating agent.

The iminothiazolidine compound (VII) may be obtained by reacting the thiourea (XXVI) with the halide (XXVII) to give the iminothiazoline (XXVIII) which is then treated with the compound (V), (XIV) or (VI) under the same condition as described in Procedure (B).

The iminothiazolidine compound (VII) can also be produced by treating the thiourea (XXX) with the halide (XXVII).

The compound (IV) can be obtained by hydrolyzing the compound (I-4) with an acid.

This reaction is usually carried out in a solvent at a temperature of about 30° to 200° C. for a period of 1 to 100 hours. The acid may be used at proportions of 1 to 1000 equivalents to one equivalent of the compound (I-4).

Examples of the solvent are aromatic hydrocarbons (e.g., benzene, toluene, xylene), ethers (e.g., diethyl ether, diisopropyl ether, dioxane, tetrahydrofuran, diethylene glycol dimethyl ether), fatty acids (e.g., formic acid, acetic acid, oleic acid), alcohols (e.g., methanol, ethanol, isopropanol, t-butanol, octanol, cyclohexanol, 2-methoxyethanol, diethylene glycol, glycerin) and water. These solvents may be used solely or in combination. Examples of the acid are sulfuric acid and hydrochloric acid which is preferred.

After completion of the reaction, the reaction mixture may be subjected to ordinary post-treatment in the same manner as described in Procedure (A) to give the compound (IV).

Alternatively, after completion of the reaction, the reaction mixture may be concentrated under reduced pressure to give the base of the compound (IV). Although the compound (IV) is obtained by neutralization of the base, it is possible to use the base as such in Procedure (B) without converting into the compound (IV).

Typical examples of the compound (IV) obtained by the above procedure are shown in Table 2.

TABLE 2

(IV)

$R^1, R^4$ — phenyl — N = C(NH) — S — C(=)—$CH_2R^6$

| $R^1$ | $R^6$ | $R^4$ |
|---|---|---|
| $CF_3$ | H | 4-F |
| $CF_3$ | $CH_3$ | 4-F |
| $CF_3$ | H | 5-F |
| $CF_3$ | $CH_3$ | 5-F |
| $CF_3$ | H | 4-Cl |
| $CF_3$ | H | 2-F |
| F | H | 6-F |
| Cl | H | 5-F |
| Br | $CH_3$ | 4-F |
| $OCF_3$ | H | 4-F |

For the practical usage of the iminothiazoline compounds (I), they are usually formulated with conventional solid or liquid carriers or diluents as well as surface active agents, or other auxiliary agents into conventional formulations such as emulsifiable concentrates, wettable powders, flowables, granules and water-dispersible granules.

These formulations contain the iminothiazoline compounds (I) as an active ingredient at a content within the range of about 0.02% to 90% by weight, preferably of about 0.05% to 80% by weight.

Examples of the solid carrier or diluent are fine powders or granules of kaolin clay, attapulgite clay, bentonite, terra alba, pyrophyllite, talc, diatomaceous earth, calcite, walnut shell powders, urea, ammonium sulfate and synthetic hydrous silica. As the liquid carrier or diluent, there may be exemplified aromatic hydrocarbons (e.g., xylene, methylnaphthalene), alcohols (e.g., isopropanol, ethylene glycol, 2-ethoxyethanol), ketones (e.g., acetone, cyclohexanone, isophorone), vegetable oils (e.g., soybean oil, cotton seed oil), dimethylsulfoxide, N,N-dimethylformamide, acetonitrile and water.

The surface active agent used for emulsification, dispersing or spreading may be of any type, for instance, either anionic or non-ionic. Examples of the surface active agent include alkylsulfates, alkylsulfonates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymer, sorbitan fatty acid esters and polyoxyethylene sorbitan fatty acid esters. Examples of the auxiliary agent include ligninsulfonates, alginates, polyvinyl alcohol, gum arabic, CMC (carboxymethyl cellulose) and PAP (isopropyl acid phosphate).

The iminothiazoline compounds (I) are usually formulated in any suitable formulation and used for pre-emergence or post-emergence control of undesired weeds by soil treatment, foliar treatment or flood fallowing treatment. These treatments include application to the soil surface prior to or after planting, incorporation into the soil prior to planting or transplanting, and the like. The foliar treatment may be effected by spraying a herbicidal composition containing the iminothiazoline compounds (I) over the top of plants. It may also be applied directly to the weeds if care must be taken to keep the chemical off the crop foliage.

The dosage of the iminothiazoline compounds (I) may vary depending on the prevailing weather conditions, formulation used, prevailing season, mode of application, soil involved, crop and weed species, and the like. Usually, however, the dosage is from about 10 to 5000 grams, preferably from about 20 to 2000 grams, of the active ingredient per hectare. The herbicidal composition thus formulated in the form of an emulsifiable concentrate, wettable powder or flowable may usually be employed by diluting it with water at a volume of about 100 to 1000 liters per hectare, if necessary, with addition of an auxiliary agent such as a spreading agent. The herbicidal composition formulated in the form of granules may usually be applied as such without dilution.

Examples of the spreading agent include, in addition to the surface active agents as described above, polyoxyethylene resin acid (ester), ligninsulfonate, abietylenic acid salt, dinaphthylmethanedisulfonate and paraffin.

The iminothiazoline compounds (I) are useful as a herbicide to be employed for paddy filed, crop field, orchards, pasture land, lawns, forests and non-agricultural fields. Further, the iminothiazoline compounds (I) may also be used together with any other herbicide to improve their herbicidal activity, and in some cases, synergistic effects can be expected. Furthermore, these compounds may be applied in combination with insecticides, acaricides, nematocides, fungicides, plant growth regulators, fertilizers, soil improvers and the like.

The present invention will be explained in more detail by way of Preparation Examples, Reference Examples, Formulation Examples and Test Examples, to which however the invention is not limited in any way.

Practical and presently preferred embodiments for production of the iminothiazoline compounds (I) are illustrated in the following examples.

Preparation Example 1

Procedure (A)

A mixture of acetyl chloride (2.75 g) and acetonitrile (70 ml) was cooled at 0° C., and potassium thiocyanate (3.57 g) was added to this mixture, followed by stirring at room temperature for 6 hours. After cooling at 0° C., 3-trifluoromethyl-4-fluoro-N-propalgylaniline (7.6 g) was added to the reaction mixture and stirring was continued at room temperature for 3 hours.

After removal of the solvent under reduced pressure, the concentrated residue was extracted with ethyl acetate (300 ml), and the extract was washed with water. After removal of the solvent, crystallines (8.5 g) were obtained. These crystallines were slowly added to sulfuric acid (25 ml) at 0° C., and stirring was continued at 0° C. for 0.5 hours, then at room temperature for 1 hour. The reaction solution was poured into ice water, and the mixture was neutralized with aqueous sodium hydroxide to give 8 g of 2-acetylimino-3-(3-trifluoromethyl-4-fluorophenyl)-5-methylthiazoline (Compound No. 1). m.p., 179.0° C.

Preparation Example 2

Procedure (B)

To a mixture of 2-imino-3-(3-trifluoromethyl-4-fluorophenyl)- 5-methylthiazoline hydrochloride (0.62 g) and triethylamine (0.61 g) in ethyl acetate (20 ml), trifluoroacetic acid anhydride (0.42 g) was added at 0° C. After stirring at room temperature for 3 hours, the residue was extracted with ethyl acetate (100 ml), and the extract was washed with water. The solvent was removed under reduced pressure to give crystallines. These crystallines were washed with hexane to give 0.45 g of 2-trifluoroacetylimino- 3-(3-trifluoromethyl-4- fluorophenyl )-5-methylthiazoline (Compound No.2). m.p., 119.4° C.

In the same manner as above, the iminothiazoline compounds (I) as shown in Table 3 were obtained.

TABLE 3

(I)

structure as shown with phenyl ring bearing $R^1$, $R^4$ substituents attached via N to a thiazoline ring with $R^2$ on carbon and $R^3$ on ring N

| Compound No. | $R^1$ | $R^2$ | $R^3$ | $R^4$ | m.p. (°C.) |
|---|---|---|---|---|---|
| 1 | $CF_3$ | $CH_3$ | $COCH_3$ | 4-F | 179.0 |
| 2 | $CF_3$ | $CH_3$ | $COCF_3$ | 4-F | 119.4 |
| 3 | $CF_3$ | $CH_3$ | $CO$-i-$C_3H_7$ | 4-F | 133.2 |
| 4 | $CF_3$ | $CH_3$ | $CO_2$-i-$C_3H_7$ | 4-F | 130.8 |
| 5 | $CF_3$ | $CH_3$ | $COCF_3$ | 6-F | 144.7 |
| 6 | $CF_3$ | $CH_3$ | $CO_2$-i-$C_3H_7$ | 6-F | 158.5 |
| 7 | $CF_3$ | $CH_3$ | $COCH_3$ | 4-Cl | 187.9 |
| 8 | $CF_3$ | $CH_3$ | $COCF_3$ | 4-Cl | 134.2 |
| 9 | $CF_3$ | $CH_3$ | CO-cyclopropyl  | 4-Cl | 166.2 |
| 10 | $CF_3$ | $CH_3$ | $COCHF_2$ | 4-F | 139.9 |
| 11 | $CF_3$ | $C_2H_5$ | $COCH_3$ | 4-F | 131.4 |
| 12 | $CF_3$ | $C_2H_5$ | $COCF_3$ | 4-F | 84.6 |
| 13 | $CF_3$ | $C_2H_5$ | $COCHF_2$ | 4-F | 117.0 |
| 14 | Cl | Br | $CO_2C_2H_5$ | 4-F | 224.1 |
| 15 | $CF_3$ | $CH_3$ | $COCH_2$-t-$C_4H_9$ | 4-F | 129.3 |
| 16 | $CF_3$ | $CH_3$ | CO-n-$C_5H_{11}$ | 4-F | 46.3 |
| 17 | $CF_3$ | $CH_3$ | $COCH_2CH_2Cl$ | 4-F | 35.0 |
| 18 | $CF_3$ | $CH_3$ | $COCH_2OCH_3$ | 4-F | 121.5 |
| 19 | $CF_3$ | $CH_3$ | CO-cyclohexyl 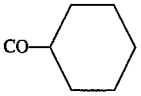 | 4-Cl | 103.0 |

TABLE 3-continued $$\text{(I)}$$

Structure: phenyl ring with $R^1$, $R^4$ substituents, attached to N—CH=C(R²)—S—C(=N-R³) forming an iminothiazoline.

| Compound No. | $R^1$ | $R^2$ | $R^3$ | $R^4$ | m.p. (°C.) |
|---|---|---|---|---|---|
| 20 | $CF_3$ | $CH_3$ | $COC_3F_7$ | 4-Cl | 87.7 |
| 21 | $CF_3$ | $CH_3$ | $SO_2CF_3$ | 4-Cl | 150.0 |
| 22 | $CF_3$ | $CH_3$ | $CO_2$-n-$C_6H_{13}$ | 4-F | oil |
| 23 | $CF_3$ | $CH_3$ | CO-cyclopropyl-CH₃ | 4-F | 134.4 |
| 24 | $CF_3$ | $CH_3$ | $SO_2CH_3$ | 4-Cl | 144.2 |
| 25 | $CF_3$ | $CH_3$ | $CO_2CH_2CH_2OCH_3$ | 4-Cl | 112.1 |

The compounds (1) and (7) were produced according to the method of Preparation Example 1, whereas the method of Preparation Example 2 was used for production of the other compounds.

Preparation Example 3

(i) A mixture of 2-acetylimino-3-(3-trifluoromethyl-4-fluorophenyl)-5-methylthiazoline (3.5 g) and hydrochloric acid (36%, 3.5 ml) in ethanol-water (35 ml) was refluxed for 3 hours. After cooling, the solvent was removed under reduced pressure, and the residue was isolated and washed with a little amount of iso-propanol and hexane to give 2.8 g of 3-(3-trifluoromethyl-4-fluorophenyl)-5-methyl-2-iminothiazoline hydrochloride (compound (i)).

(ii) To a mixture of ethyl acetate (50 ml) and aqueous potassium carbonate (20 ml), 3-(3-trifluoromethyl-4-fluorophenyl)- 5-methyl-2-iminothiazoline hydrochloride (1 g) was added; and the mixture was stirred. The organic layer was isolated and dried over anhydrous magnesium sulfate. The solvent was removed under reduced pressure to give 0.7 g of 3-(3-trifluoromethyl-4-fluorophenyl)-5-methyl-2-iminothiazoline as an oil.

In the same manner as above, the iminothiazoline compounds (IV) as shown in Table 4 were obtained.

TABLE 4

| Compound No. | $R^1$ | $R^4$ | $R^6$ | $^1$H-NMR/d$^6$-DMSO |
|---|---|---|---|---|
| i | $CF_3$ | 4-F | H | 10.1 (bs, 2H)<br>8.3–7.5 (m, 3H)<br>7.3 (s, 1H)<br>2.3 (s, 3H) |
| ii | $CF_3$ | 4-Cl | H | 10.1 (bs, 2H)<br>8.2–7.7 (m, 3H)<br>7.3 (s, 1H)<br>2.3 (s, 3H) |

The following illustrates practical embodiments of the herbicidal composition according to the present invention wherein parts are by weight. The compound number of the active ingredient corresponds to that of Table 3.

Formulation Example 1

Fifty parts of any one of Compound Nos. 1 to 21 and 23 to 25, 3 parts of calcium ligninsulfonate, 2 parts of sodium laurylsulfate and 45 parts of synthetic hydrous silica are well mixed while being powdered to obtain wettable powder.

Formulation Example 2

Five parts of any one of Compound Nos. 1 to 25, parts of "Toxanone P8L®" (commercially available surface active agent; Sanyo Kasei K. K.) and 80 parts of cyclohexanone are well mixed to obtain emulsifiable concentrate.

Formulation Example 3

Two parts of any one of Compound Nos. 1 to 21 and 23 to 25, 1 part of synthetic hydrous silica, 2 parts of calcium ligninsulfonate, 30 parts of bentonite and 65 parts of kaolin clay are well mixed while being powdered. The mixture is then kneaded with water, granulated and dried to obtain granules.

Formulation Example 4

Twenty-five parts of any one of Compound Nos. 1 to 21 and 23 to 25 are mixed with 3 parts of polyoxyethylene sorbitan monooleate, 3 parts of carboxymethyl cellulose (CMC) and 69 parts of water and pulverized until the particle size of the mixture becomes less than 5 microns to obtain a suspension.

The biological data of the iminothiazoline compound (I) as the herbicide will be illustrated in the following Test Examples wherein the phytotoxicity to crop plants and the herbicidal activity on weeds were determined by visual observation as to the degree of germination as well as the growth inhibition and rated with an index 0, 1, 2, 3, 4, 5, 6, 7, 8, 9 or 10, the numeral "0" indicating no material difference as seen in comparison with the untreated plants and the numeral "10" indicating the complete inhibition or death of the test plants. The compound number in the biological data corresponds to that shown in Table 3.

The compounds as shown in Table 5 were used for comparison.

TABLE 5

| Compound No. | Structure | Remarks |
|---|---|---|
| A | Cl—C₆H₄—CH₂SC(=O)—N(C₂H₅)₂ | Benthiocarb (commercially available herbicide) |
| B | 3-F-C₆H₄—N(CH=CH—S—)C=N—C(=O)OC₂H₅ (iminothiazoline structure) | EP-A-0349282 |

TABLE 5-continued

| Compound No. | Structure | Remarks |
|---|---|---|
| C | [structure: 3-ethoxyphenyl group attached to N of a thiazoline ring with N-C(=N)-S, bearing N-C(=O)OC₂H₅] | EP-A-0349282 |

Test Example 1

Cylindrical plastic pots (diameter, 10 cm; height, cm) were filled with upland field soil, and the seeds of japanese millet, tall morningglory and velvetleaf were sowed therein and covered with soil. A designated amount of the test compound formulated in an emulsifiable concentrate as in Formulation Example 2 was diluted with water, and the dilution was sprayed onto the soil surface by means of a small hand sprayer at a spray volume of 1000 liters per hectare. The test plants were grown in a greenhouse for days, and the herbicidal activity was examined. The results are shown in Table 6.

TABLE 6

| Compound No. | Dosage (g/ha) | Herbicidal activity | | |
|---|---|---|---|---|
| | | Japanese millet | Tall morning-glory | Velvet-leaf- |
| 1 | 2000 | 10 | 10 | 7 |
|   | 500  | 10 | 10 | 7 |
| 2 | 2000 | 10 | 10 | 10 |
|   | 500  | 10 | 10 | 10 |
| 3 | 2000 | 10 | 10 | 10 |
|   | 500  | 10 | 10 | 10 |
| 4 | 2000 | 10 | 10 | 10 |
|   | 500  | 10 | 10 | 10 |
| 5 | 2000 | 7  | 7  | 7 |
| 7 | 2000 | 9  | 10 | 7 |
| 8 | 500  | 9  | 10 | 10 |
| 9 | 500  | 7  | 8  | 7 |
| 10| 500  | 10 | 10 | 10 |
| 11| 500  | 10 | 10 | 10 |
| 12| 500  | 10 | 10 | 10 |
| 13| 500  | 10 | 10 | 10 |
| 15| 2000 | 9  | 9  | 8 |
|   | 500  | 9  | 8  | 8 |
| 16| 2000 | 9  | 10 | — |
| 18| 2000 | 10 | 10 | 10 |
| 23| 500  | 9  | 9  | 8 |
| 25| 2000 | 9  | 10 | 7 |
| A | 2000 | 7  | 0  | 0 |
|   | 500  | 0  | 0  | 0 |
| B | 2000 | 0  | 0  | 0 |
| C | 2000 | 0  | 0  | 0 |

Test Example 2

Cylindrical plastic pots (diameter, 10 cm; height, cm) were filled with upland field soil, and the seeds of japanese millet, morningglory, radish and velvetleaf were sowed therein and cultivated in a greenhouse for 10 days. A designated amount of the test compound formulated in an emulsifiable concentrate as in Formulation Example 2 was diluted with water containing a spreading agent, and the dilution was sprayed over the foliage of the test plant by means of a small hand sprayer at a spray volume of 1000 liters per hectare. The test plants were further grown in the greenhouse for 20 days, and the herbicidal activity was examined. The results are shown in Table 7.

TABLE 7

| Compound No. | Dosage (g/ha) | Herbicidal activity | | | |
|---|---|---|---|---|---|
| | | Japanese millet | Morning-glory | Radish | Velvet-leaf- |
| 1 | 2000 | 9 | 10 | 10 | 9 |
|   | 500  | 9 | 10 | 10 | 8 |
| 2 | 2000 | 9 | 10 | 10 | 10 |
|   | 500  | 9 | 10 | 10 | 10 |
|   | 125  | 9 | 10 | 10 | 10 |
| 3 | 2000 | 9 | 10 | 10 | 9 |
|   | 500  | 9 | 10 | 10 | 9 |
|   | 125  | 8 | 10 | 9  | 9 |
| 4 | 2000 | 9 | 10 | 10 | 10 |
|   | 500  | 9 | 10 | 10 | 10 |
|   | 125  | 9 | 10 | 10 | 10 |
| 7 | 2000 | 9 | 9  | 10 | 7 |
|   | 500  | 9 | 9  | 10 | 7 |
| 8 | 500  | 9 | 9  | 10 | 9 |
|   | 125  | 9 | 9  | 10 | 9 |
| 9 | 500  | 9 | 10 | 10 | 9 |
| 10| 500  | 9 | 10 | 10 | 10 |
|   | 125  | 9 | 10 | 10 | 10 |
| 11| 500  | 9 | 10 | 10 | 9 |
| 12| 500  | 10| 10 | 10 | 10 |
|   | 125  | 10| 10 | 10 | 10 |
| 13| 500  | 10| 10 | 10 | 10 |
|   | 125  | 9 | 10 | 10 | 10 |
| 14| 2000 | — | 9  | 10 | — |
| 15| 2000 | 10| 9  | 10 | 9 |
|   | 500  | 10| 10 | 10 | 9 |
| 16| 2000 | 10| 9  | 10 | 8 |
|   | 500  | 9 | 10 | 10 | 7 |
| 17| 2000 | 10| 9  | 10 | 7 |
| 18| 2000 | 10| 10 | 10 | 8 |
| 19| 2000 | 10| 10 | 10 | 7 |
| 20| 2000 | 9 | 10 | 9  | 7 |
| 21| 2000 | — | 10 | —  | — |
| 22| 2000 | 10| 10 | 10 | 10 |
|   | 500  | 7 | 10 | 9  | 10 |
| 23| 500  | 10| 10 | 10 | 8 |
|   | 125  | 9 | 10 | 10 | 8 |
| 25| 2000 | 9 | 10 | 10 | 10 |
|   | 500  | 7 | 10 | 10 | 7 |
| A | 2000 | 9 | 2  | 1  | 0 |
|   | 500  | 3 | 1  | 0  | 0 |
| B | 2000 | 1 | 3  | 0  | 0 |
|   | 500  | 0 | 1  | 0  | 0 |
| C | 2000 | 0 | 2  | 1  | 0 |
|   | 500  | 0 | 1  | 0  | 0 |

Test Example 3

Cylindrical plastic pots (diameter, 8 cm; height, cm) were filled with paddy filed soil, and the seeds of barnyardgrass (*Echinochloa oryzicola*) and hardstem bulrush (*Scirpus juncoides*) were sowed in 1 to 2 cm depth. Water was poured therein to make a flooded condition, and rice Seedlings of 2-leaf stage were transplanted therein, and the test plants were grown in a greenhouse. Six days (at that time seeds began to germinate) thereafter, a designated amount of the test compound formulated in an emulsifiable concentrate as in Formulation Example 2 and diluted with water (2.5 ml) was applied to the pots by perfusion. The test plants were grown for an additional 19 days in the greenhouse, and the herbicidal activity and phytotoxicity were examined. The results are shown in Table 8.

TABLE 8

| Compound No. | Dosage (g/ha) | Phytotoxicity Rice plant | Herbicidal activity | |
|---|---|---|---|---|
| | | | Barnyard-grass | Hardstem bulrush |
| 1 | 63 | 1 | 9 | 9 |
| 4 | 63 | 1 | 10 | 8 |
| 9 | 63 | 0 | 7 | 7 |
| 14 | 250 | 0 | 8 | 7 |
| 18 | 16 | 1 | 9 | 9 |
| A | 250 | 0 | 7 | 3 |
| | 63 | 0 | 2 | 0 |
| B | 250 | 0 | 0 | 0 |
| C | 250 | 0 | 0 | 0 |

Test Example 4

Vats (33 cm×23 cm×11 cm) were filled with upland field soil, and the seeds of cotton, tall morningglory, black nightshade, giant foxtail, barnyardgrass and johnsongrass were sowed therein 1 to 2 cm depth. A designated amount of the test compound formulated in an emulsifiable concentrate as in Formulation Example 2 was diluted with water, and the dilution was sprayed onto the soil surface by means of a small hand sprayer at a spray volume of 1000 liters per hectare. The test plants were grown in a greenhouse for 20 days, and the herbicidal activity and phytotoxicity were examined. The results are shown in Table 9.

TABLE 9

| Compound No. | Dosage (g/ha) | Phytotoxicity Cotton | Herbicidal activity | | | | |
|---|---|---|---|---|---|---|---|
| | | | Tall morning-glory | Black night-shade | Giant foxtail | Barn-yard-grass | John-son-grass |
| 1 | 500 | 0 | 10 | 10 | 10 | 10 | 10 |
| 2 | 500 | 0 | 10 | 10 | 10 | 10 | 8 |
| 3 | 500 | 0 | 10 | 9 | 10 | 10 | 8 |
| 7 | 500 | 0 | 10 | — | 10 | 9 | 8 |
| 8 | 500 | 0 | 10 | 10 | 10 | 9 | 8 |
| 9 | 500 | 0 | 8 | 7 | 10 | 7 | 7 |
| 10 | 500 | 0 | 10 | 9 | 10 | 10 | 10 |
| 11 | 500 | 0 | 10 | — | 10 | 10 | 10 |
| 15 | 250 | 0 | 7 | 7 | 9 | 7 | 8 |
| 16 | 500 | 0 | 7 | 8 | 10 | 8 | 10 |
| 18 | 250 | 0 | 7 | 7 | 10 | 7 | 9 |
| 25 | 500 | 0 | 7 | 10 | 9 | 7 | — |
| A | 500 | 0 | 0 | 0 | 6 | 6 | 0 |
| B | 500 | 0 | 0 | 0 | 0 | 0 | 0 |
| C | 500 | 0 | 0 | 0 | 0 | 0 | 0 |

Test Example 5

Wagner's pots (1/5000 are) were filled with paddy field soil, and the seeds of barnyardgrass (*Echinochloa oryzicola*) and broad-leaved weeds (i.e., common falsepimpernel, indian toothcup, waterwort, *Ammannia multiflora*) were sowed in 1 to 2 cm depth. Water was poured therein to make a flooded condition, and rice seedling of 3-leaf stage were transplanted therein, and the teast plants were grown in a greenhouse. Five days (at that time barnyardgrass began to germinate) thereafter, a designated amount of the test compound formulated in an emulsifiable concentrate as in Formulation Example 2 and diluted with water (10 ml) was applied to the pots by perfusion. The test plants were grown for an additional 19 days in the greenhouse, and the herbicidal activity and phytotoxicity were examined. The results are shown in Table 10. At the time of the treatment, the depth of water in the pots was kept at 4 cm and following two days, water was let leak a volume corresponding to a 3 cm depth per day.

TABLE 10

| Compound No. | Dosage (g/ha) | Phytotoxicity Rice plant | Herbicidal activity | |
|---|---|---|---|---|
| | | | Barnyard-grass | Broad-leaved weeds |
| 2 | 63 | 1 | 9 | 9 |
| 7 | 63 | 0 | 9 | 10 |
| 8 | 16 | 0 | 9 | 10 |
| 9 | 63 | 0 | 9 | 10 |
| | 16 | 0 | 8 | 8 |
| 11 | 16 | 0 | 10 | — |
| 12 | 16 | 0 | 7 | 9 |
| 13 | 16 | 1 | 7 | 10 |
| 14 | 250 | 0 | 8 | — |
| 15 | 63 | 1 | 10 | 10 |
| 16 | 63 | 1 | 8 | 9 |
| | 16 | 0 | 8 | 7 |
| 19 | 250 | 1 | 10 | 10 |
| | 63 | 0 | 8 | 7 |
| 20 | 250 | 1 | 8 | 10 |
| 22 | 63 | 0 | 9 | — |
| 23 | 16 | 1 | 9 | — |
| 25 | 250 | 1 | 10 | 10 |
| | 63 | 0 | 9 | 8 |
| A | 250 | 0 | 7 | 0 |
| | 63 | 0 | 0 | 0 |
| B | 250 | 0 | 0 | 0 |
| C | 250 | 0 | 0 | 0 |

Test Example 6

Vats (33 cm×23 cm×11 cm) were filled with upland field soil, and the seeds of persian speedwell and wheat were sowed therein 1 to 2 cm depth. A designated amount of the test compound formulated in an emulsifiable concentrate as in Formulation Example 2 was diluted with water, and the dilution was sprayed onto the soil surface by means of an automatic sprayer at a spray volume of 1000 liters per hectare. The test plants were grown in a greenhourse for 25 days, and the herbicidal activity and phytotoxicity were examined. The results are shown in Table 11.

TABLE 11

| Compound No. | Dosage (g/ha) | Phytotoxicity Wheat | Herbicidal activity Persian speedwell |
|---|---|---|---|
| 1 | 32 | 0 | 10 |
| 2 | 32 | 0 | 10 |
| 4 | 32 | 0 | 9 |
| 7 | 32 | 0 | 7 |
| 8 | 32 | 0 | 10 |
| 9 | 125 | 0 | 10 |
| 15 | 250 | 1 | 10 |
| 16 | 250 | 0 | 10 |
| B | 250 | 0 | 0 |
| C | 250 | 0 | 0 |

What is claimed is:

1. An iminothiazoline compound of the formula:

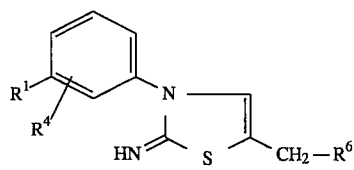

(IV)

wherein $R^1$ is halogen, halo(lower)alkyl, halo(lower)alkoxy or halo(lower)alkylthio; $R^4$ is halogen; and $R^6$ is hydrogen or methyl.

2. An iminothiazoline compound of the formula:

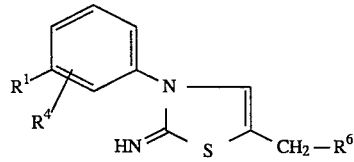

(IV)

wherein $R^1$ is halogen, halo $(C_1-C_3)$alkyl, halo$(C_1-C_3)$alkoxy or halo $(C_1-C_3)$alkylthio; $R^4$ is halogen; and $R^6$ is hydrogen or methyl.

3. The compound of claim 1, wherein $R^1$ is selected from the group consisting of trifluoromethyl, fluoro, chloro, bromo and trifluoromethoxy; and $R^4$ is fluoro or chloro.

4. The compound of claim 1, wherein $R^1$ is trifluoromethyl, $R^4$ is 4-fluoro and $R^6$ is hydrogen.

5. The compound of claim 1, wherein $R^1$ is trifluoromethyl, $R^4$ is 4-chloro and $R^6$ is hydrogen.

* * * * *